(12) United States Patent
Bracht

(10) Patent No.: US 7,175,853 B1
(45) Date of Patent: Feb. 13, 2007

(54) THERAPEUTIC SYSTEM WHICH CAN BE MOISTURE-ACTIVATED

(75) Inventor: Stefan Bracht, Ochtendung (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 09/647,289

(22) PCT Filed: Mar. 18, 1999

(86) PCT No.: PCT/EP99/01802

§ 371 (c)(1),
(2), (4) Date: Nov. 15, 2000

(87) PCT Pub. No.: WO99/49853

PCT Pub. Date: Oct. 7, 1999

(30) Foreign Application Priority Data

Mar. 30, 1998 (DE) .................. 198 14 087

(51) Int. Cl.
*A61F 13/00* (2006.01)
*A61F 13/02* (2006.01)
*A61L 15/16* (2006.01)

(52) U.S. Cl. .................. 424/449; 424/448; 424/443; 424/446; 424/447

(58) Field of Classification Search ............. 424/484, 424/486, 489, 443, 449, 448
See application file for complete search history.

(56) References Cited

U.S. PATENT DOCUMENTS

| 4,781,924 A | 11/1988 | Lee et al. |
| 4,837,027 A | 6/1989 | Lee et al. |
| 5,215,751 A | 6/1993 | Müller et al. |
| 5,230,898 A | 7/1993 | Horstmann et al. |
| 5,466,466 A | 11/1995 | Müller et al. |
| 5,702,721 A | 12/1997 | Horstmann et al. |
| 5,807,570 A * | 9/1998 | Chen et al. .................. 424/449 |

FOREIGN PATENT DOCUMENTS

| DE | 39 05 050 | 8/1990 |
| DE | 39 05 051 | 8/1990 |
| DE | 39 10 543 | 10/1990 |
| DE | AT 392 587 B | 4/1991 |
| EP | 249 343 | 12/1987 |
| EP | 0 316 065 | 5/1989 |
| GB | 2290964 | 1/1996 |
| WO | WO 94/07468 | 4/1994 |
| WO | WO 97/11696 | 4/1997 |

* cited by examiner

*Primary Examiner*—Isis Ghali
(74) *Attorney, Agent, or Firm*—Frommer Lawrence & Haug LLP

(57) ABSTRACT

This invention provides for a therapeutic system for timed and controlled release of at least one therapeutic active agent to a human or animal organism by diffusion through the skin or mucous membrane. The active agent is initially present, for the purposes of manufacture and storage, in a first state in the form of a pharmaceutically acceptable salt, which is chemically stable and insufficiently permeable for the skin or mucous membrane. The active agent is converted at the application site upon access of moisture and by an activating agent into a second state, which is suitable for diffusion through the skin or mucous membrane and in which it is taken up by the organism. The activating agent is initially present as a solid substance or a mixture or a plurality of such substances, which reacts in aqueous solution as an acid or base. The activating agent contains a portion of water of at least 5% in its solid body structure, either intercalated or bound thereto.

29 Claims, 11 Drawing Sheets

THERAPEUTIC SYSTEM WHICH CAN BE MOISTURE-ACTIVATED

This application is a 371 of PCT/EP99/01802 filed Mar. 18, 1999. This application claims priority to German application No. 198 14 087.8 filed Mar. 30, 1998.

This invention relates to a therapeutic system for timed and quantity-controllable release of at least one therapeutically active substance to a human or animal organism by means of diffusion through the skin or mucous membrane, with said active substance, for manufacture and storage, being initially present in a first state in which it is chemically stable and Insufficiently permeable for the skin or mucous membrane, whereas at the site of application it is converted into a second state by access of moisture, in which state it is suitable for diffusion through the skin or mucous membrane and taken up by the organism.

Grounds for utilising an activatable system exist in all those cases where that chemical state of an active sub stance which is most suitable for delivery to the body is not identical with the state which is optimally suitable for the production and storage of a therapeutics system.

Therapeutic systems activated by moisture are known and have bee described, for example, in U.S. Pat. No. 4,781,924; EP 0 316 065 B1; DE 38 81 340.

Only part of these documents relate to moisture-activated systems in which activation involves the chemical con version of the active agent.

These comprise, for instance, systems wherein active substance is initially present in a state which is not capable of diffusing through the surface of the system in quantities per unit of time which are sufficient for therapeutic purposes.

Apart from the active agent it is therefore necessary to use an "activating agent" which in its first state is water-free while, under absorption of moisture, it is transferred into a second, hydrated and dissolved state. In the dissolved state, the activating agent is then capable of transforming active agent into a second form which is able to diffuse through the surface of the system in therapeutically sufficient quantities per unit of time.

Moreover, in the aforementioned documents there is described a structure of systems wherein the activator is present from the start in dissolved state but enclosed in microcapsules which in the initial state do not release the activator to the environment. Activation involves the destruction of the microcapsules, preferably by breaking or melting. Activation by skin moisture is not described for this modification. The known systems are complicated in terms of their structure and thereby cause comparatively high manufacturing costs whilst in part resulting in a dissatisfactory activation process.

Starting from the aforementioned prior art, it is the object of the present invention to simplify moisture-activatable systems and thereby to reduce production costs. It is a further aspect of the object to accelerate the activation process, as well as to attain an increase of the release rate of active substance from such systems.

These objects are surprisingly achieved according to the present invention, a therapeutic system for timed and controlled release of at least one therapeutic active agent to a human or animal organism by means of diffusion through the skin or mucous membrane, said active agent initially being present, for the purposes of manufacture and storage, in a first state in which it is chemically stable and insufficiently permeable for the skin or mucous membrane, whereas it is converted at the application site into a second state by access of moisture, in which state it is suitable for diffusion though the skin or mucous membrane and in which it is taken up by the organism, characterized in that said active agent in said first state is contained in the system as a pharmaceutically acceptable salt which upon access of moisture and by means of an activating agent, which is likewise contained in the system, is chemically converted into the said second state of an acid or base which is taken up through the skin or mucous membrane into the organism in an accelerated manner and in greater quantities compared to the salt form, said activating agent being a solid substance reacting in aqueous solution as an acid or base, or a mixture of a plurality of such substances, and containing a portion of water of at least 5% in its solid body structure, either intercalated or bound thereto. Due to the activator being present in the system neither in the water-free nor in the dissolved state, but instead being employed in a hydrated but undissolved chemical state, preferably in the form of the hydrates of the activator, these hydrates possess a crystalline state of order and, in this state, entrain water in a defined quantity ratio in addition to the activator. This hydrated form of the activator is present in the system as an undissolved solid. This undissolved form is practically incapable of converting the active substance from a first chemical state into a second one. It is dissolved only upon access of skin moisture and then becomes active with respect to the active substance in the desired manner. By the water which is entrained within the crystal of the activator from the start, the process of activation is accelerated and markedly improved in its overall extent.

The system according to the invention is preferably used in the manufacture of transdermal therapeutic systems (TTSs). Since the activator is inactive in the undissolved state, it is even possible to incorporate active agent and activator in one and the same layer of a TTS, which layer may at the same time also possess pressure-sensitive adhesive properties.

Especially by means of this latter "drug-in-adhesive" structure, it is possible to release the active substance astonishingly quickly and in large amounts, even if the water-free forms of the activator are utilised.

In this way it is possible to realise simplified TTS structures while at the same time enabling accelerated and increased active substance delivery.

The changeable chemical states specifically concern the acid-base equilibrium in which the active substance in question is present.

Among the active agents used there is a large number of compounds containing acidic or basic reacting molecule groups; the great majority of these have basic characteristics.

The basic groups are typically primary, secondary or tertiary amines. These functional groups are reactive and can take part in a plurality of reactions (e.g. oxidation processes) which are apt to result in degradation of the active substance.

If these groups are transformed into a salt by reacting with an acid, this very frequently leads to a marked improvement of chemical stability.

Furthermore, the salts generally have higher melting points than the free bases. It is even possible for a base which is present as a liquid at room temperature to be transformed into the solid state by conversion into a salt. Apart from raising the melting point, salt formation always results in a reduction of volatility.

Finally, salt formation practically always leads to a marked increase in the water-solubility whereas, in parallel thereto, there occurs a clear reduction in the solubility in organic solvents.

The aforementioned properties of the salts of basic active agents lead to the fact that in pharmaceutics research and development, in a great majority of cases the salt of a basic active substance is given preference as a raw material to the free base.

For the development of TTSs this often affords an advantage due to the higher stability of the salts.

Of particular significance are, however, also the increased melting point and the diminished volatility of the salt form, especially since many processes for the manufacture of TTSs always include one segment involving markedly increased operating temperature typically in the range of between 60 and 120° C.

Where solvent-containing coating methods are employed, this is the drying step for removing the solvents required in the process. In the case of the solvent-free hot-melt process, the product mass is temporarily heated strongly in order to reduce viscosity.

As a consequence, in the production of TTSs there are very likely to occur problems where a low-melting and/or volatile active agent in the form of a free base is used. The salt forms offer considerable advantages in this respect.

In light of the aforementioned aspects, it is frequently desirably in TTS development to process an active agent in its salt form.

However, the active substance salts are little suited for transcutaneous administration, as compared to the non-salt forms. For example, the barrier of the human skin is predominantly of lipophile character. The skin is thus almost impermeable to strongly polar, water-soluble compounds, which is why the conversion of an active agent to a salt is in almost all cases accompanied by a deterioration of the absorption via the skin.

This frequently leads to contradictory demands being placed on the active substance which cannot be met by one of its chemical states alone.

A solution to the problem are activatable forms of TTSs. Activation of a TTS in this context means that the salt form of the active substance contained in the TTS is used, which is favourable with respect to processing and storage, and that this salt is converted into the non-salt form, which is characterized by its better ability to permeate the skin, only upon the later application of the TTS and under certain external influences. Among the possible external influences, the absorption of moisture after application to the skin surface is taken into consideration with preference.

The human skin releases moisture in two ways: Through the outermost skin layer, called epidermis, there takes place a continuous, passive escape of water vapour caused by diffusion—the transepidermal loss of water. Via the sweat glands, water vapour is, by contrast, released actively, and in the case of more intense perspiration, water even emerges in liquid form from the skin surface.

A TTS which is applied to the skin is subjected to this emerging skin moisture, and, depending on its constitution, may absorb smaller or greater amounts of moisture.

Important in this respect is the outer backing layer of a TTS, which faces away from the skin. The less water vapour-permeable the backing layer, the more pronounced is the accumulation of moisture retained in the TTS, until finally occlusion results.

This accumulation of moisture can be made use of for activating a chemical conversion reaction.

Two water-soluble or at least water-swellable reaction partners A and B which are present in the TTS in dry, practically undissolved form can react with each other only after access of moisture, with the substances being dissolved or at least solvated.

This principle is generally known from effervescent tablets, which only upon access of water form carbon dioxide in an acid-base reaction.

In the case of an acid-base reaction, water is required merely as solvent for the reactants. It is, however, not consumed in the reaction. A small amount of water therefore suffices to start and continuously maintain the process.

To now release the active substance, which is present in the form of a salt, from the salt in an acid-base reaction, a reaction partner is required, designated here as activator.

Therapeutic systems making use of this activation principle have already been described in the above-cited U.S. Pat. No. 4,781,924, EP 0 316 065 B1, DE 38 81 340.

However, the inventors here started from the assumption that the activating agent must be present in an expressly water-free state.

The activating agent is hydrated, or dissolved, only in a second state after having absorbed moisture during application of the system, or alternatively after having absorbed moisture from a reservoir within the system.

It was now surprisingly found that it is not necessary to store the activator in the system in a water-free form. Even if the activator is present in a hydrated, but undissolved form, almost no reaction with the active substance salt takes place during the manufacture and storage of the system Many activators which are suitable as auxiliary agents typically do not occur in water-free form at all. They must first be dried or purchased in the (frequently more expensive) water-free form, and must be stored correspondingly. This applies, for example, to the substances of sodium carbonate, sodium monohydrogen phosphate and sodium orthophosphate, which in their water-free form are even hygroscopic.

The corresponding disadvantages are not present if the hydrated forms are used.

An activator that is already present in the system in hydrated form is moreover advantageous even in respect of the course of activation upon access of moisture. It was found that when using already hydrated activators, the speed and extent of the activation process are improved as compared to the water-free activators.

This process is not to be confused with a procedure described in WO 94/07468, according to which the active substance in its water-soluble salt form and an inorganic silicate are initially mixed with each other in water, this aqueous solution is incorporated in a polymer solution and from this solution there are manufactured TTSs. After a drying step, these TTSs contain, according to the invention, the silicate in hydrated form intimately mixed with the active agent as internal disperse phase in a surrounding polymer. Here, the water-soluble active substance is according to the invention even partially dissolved in the aqueous phase of the silicate.

In contrast thereto, the systems according to the present invention comprise only structures wherein active agent and activator are present separate from each other, in a joint matrix or in different matrices. A dispersing agent is not necessarily contained.

Suitable activators with water-containing crystalline structure are inorganic or organic compounds which in aqueous solution react as an acid or base.

For converting the basic-reacting state of an active substance into the acid-reacting state, an acid-reacting activator is employed. Basic-reacting activators, by contrast, serve to transform the acid-reacting state of the active agent into the basic-reacting form.

Suitable basic-reacting activators are the following compounds (without claim to exhaustiveness):

basic silicates, basic phosphates, citrates, tartrates, succinates, basic salts of ethylenediaminetetraacetic acid, carbonates, hydrogen carbonates and hydroxides.

These compounds are utilised as alkali, alkaline earth or aluminium salts.

Also possible are compounds which are composed of more than one of the aforementioned anions and more than one of the aforementioned metal cations at the same time in a crystalline-defined mixed state. It is also possible for the aforementioned anions and cations in the crystal lattice to be combined with further ions, not mentioned here. Suitable acid-reacting activators are the following compounds (without claim to exhaustiveness):

dihydrogen phosphate, citric acid and dihydrogen citrate, tartaric acid and hydrogen tartrate, trihydrogen salts of ethylenediaminetetraacetic acid, as well as hydrogen sulfates.

These compounds are optionally used as alkali, alkaline earth or aluminium salts.

All such activators are preferably used in a form which in the crystalline state entrains defined constituent amounts of water. In one embodiment of the invention, the activating agent is a solid substance reacted in an aqueous solution as an acid or base, or a mixture of a plurality of such substances, and containing a portion of water of at least 5% in its solid body structure, either intercalated or bound thereto.

Mixtures of different activators are also possible and can be useful for adjusting a certain activation behaviour. The mixture may also comprise crystalline states of one and the same activator which contain different quantities of water, in order to modulate the activation behaviour.

Using a mixture of various activators may also be useful if the active substance is unstable when exposed to bases which are too strong. By means of the mixture it is possible in such cases to set an optimum between desired, activating, and unwanted, disintegrating influences.

The great majority of today's pharmaceutical active substances are basic whereas acid substances are the minority.

Basic active substances are very frequently used in the form of their, chemically more stable and non-volatile, water-soluble salts. These are, for instance, the hydrochlorides and sulfates.

Since the free bases generally have a greater capacity for penetrating the skin than the ionic salts, the conversion of the salts of basic active agents into the free active substance bases is of particular importance. This conversion can be performed using a basic activator in a moisture-activatable TTS.

Basic activators are therefore given special consideration in the present invention:

Among the possible basic activators, the silicates and phosphates are especially suitable.

Among the silicates, sodium metasilicate pentahydrate as well as the hydrated forms of sodium trisilicate are used preferably.

Also particularly suitable are the hydrates of magnesium trisilicate, typically the pentahydrate.

Among the phosphates, the basic monohydrogen phosphates and orthophosphates as well as the pyrophosphates are suitable. These are, in particular, disodium monohydrogen phosphate dihydrate, heptahydrate and dodecahydrate, as well as trisodium phosphate hexahydrate and dodecahydrate. Also suitable are tetrasodium diphosphate decahydrate. Furthermore, tripotassium phosphate monohydrate and trihydrate as well as magnesium hydrogen phosphate trihydrate are considered.

Of particular interest are furthermore those activators which have an internal buffer system and thus show only controlled basic reaction.

This applies especially to the compounds magnesium carbonate hydroxide and aluminium magnesium hydroxide sulfate, which, as acid-binding agents, can also be internally taken by humans. Both compounds can occur in various compositions which due to their water content in the crystal are well suited for the manufacture of the TTSs according to the present invention.

As a representative of the aluminium magnesium hydroxide sulfate, magaldrate (INN) is mentioned here. According to indications made in USP 23, this is a product of varying composition having the general formula

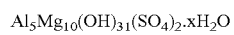

$Al_5Mg_{10}(OH)_{31}(SO_4)_2.xH_2O$

As a representative of magnesium carbonate hydroxide stands hydrotalcite (INN). According to indications in the Merck-Index (12th edition 1996), magnesium carbonate hydroxide generally is $(MgCO_3)_4\ Mg(OH)_2.5H_2O$; and hydrotalcite, in particular, is $Al_2O_3\ 6MgO\ CO_2.12H_2O$.

In addition to these examples from inorganic chemistry, the following organic-based activators are mentioned: trisodium citrate dihydrate ($C_6H_5Na_3O_7.2H_2O$), magnesium citrate tetradecahydrate ($C_{12}H_{10}Mg_3O_{14}.14H_2O$), tetrasodium edetate dihydrate ($C_{14}H_{12}N_2Na_4O_8.2H_2O$), potassium sodium tartrate tetrahydrate ($C_4H_4KNaO_6.4H_2O$) and disodium succinate hexahydrate ($C_4H_4Na_2O_4.6H_2O$).

When selecting a suitable activator, dehydrating temperatures generally play an important role. Common processes for manufacturing a TTS as a rule comprise a drying process in the case of solvent-containing coating processes, or alternatively a melting process if the TTSs are manufactured in a hot-melt process.

The temperature-dependent, complete release of water from the activator should, if possible, lie above these processing temperatures, that is, the processing temperatures should be maintained below the temperature of complete dehydration of the activator.

The difference should be at least 1–5° C., better still 5–20° C., and ideally more than 20° C.

In light of this aspect the silicates and phosphates are particularly suitable among the aforementioned activators.

The structure of moisture-activatable transdermal therapeutic systems utilising hydrated activators can be varied in many ways. This is illustrated in FIG. 1–13, which are not true to scale but show examples of layered structures.

In the most simple and at the same time preferred structure, the active agent, in a salt form suitable for manufacture and storage of the TTS, as well as the activator, in undissolved state, are present in one and the same layer of the TTS.

In another construction, active substance and activator are incorporated in separate layers.

In all cases, it is possible to implement control layers. These control layers are either inserted between the active substance and the activator, or they are disposed between the active substance and activator reservoir and the skin surface.

In the first case, the access of the activator to the active substance, after moisture absorption and dissolution, is controlled, or alternatively the access of the active substance, after moisture absorption and dissolution, to the activator.

In the second case, the release, after moisture absorption, of the active substance in its already activated, skin-penetrating form to the skin surface is controlled. Alternatively, the control layers may effect the control of the moisture absorption of the overall system or of individual layers thereof.

Suitable for control in the above sense are those layers whose water vapour-permeability is below the rate per time at which moisture is typically delivered by the skin.

To achieve an activation by moisture, in all of the aforementioned structures, water or water vapour emerging from the skin must be retained in the TTS. The backing layer of the TTS is therefore preferably adapted to be water vapour-impermeable.

This is a property, in particular, of films of polyethylene terephthalate, polyethylene, polypropylene, polyvinylchloride (PVC) and polyvinylidene chloride (PVDC), but also of those of ethylene vinyl acetate copolymer (EVA) with a preferably low portion of vinyl acetate of <10%. Films of very elastic hydrocarbon polymers such as polyisobutylene, polyisoprene, or the block copolymers of styrene and isoprene or butadiene are also possible.

As backing layer, multilayered composite materials (laminates) with only one layer thereof consisting of the polymers mentioned, may also be used.

Finally, it is also possible to use the backing layer as a control membrane by adjusting a defined, low water vapour permeability. This enables a defined retardation of the retaining of moisture, and thereby of activation.

Examples of layered structures will be described in the following with reference to the Figures.

Figure 1:
FIGS. 1–13 depict various embodiments of the therapeutic systems of the invention.

If active substance (11) and activator (12) are introduced into one layer, this layer (1), in a particularly preferred configuration, possesses pressure-sensitive adhesive properties at the same time, so that no separate adhesive layer is necessary (system A, FIG. 1).

The system A then only consists of a detachable protective layer, a pressure-sensitive adhesive layer containing active agent and activator, as well as a backing layer (2).

After application to the skin, dissolution of the activator occurs under absorption of moisture; the activator up to that moment having been present in a hydrated but undissolved state. The dissolved activator diffuses to the active substance, which is present in salt form, and transforms the same into the form of a free acid or free base. This free form diffuses through the pressure-sensitive adhesive layer to the skin and there is taken up into the body.

As an alternative, it is also possible for the active substance salt to be dissolved by the absorption of moisture and to diffuse to the activator. There, it is converted into the free acid or base of the active substance, which represents the form of the active substance which is better capable of penetrating the skin, and is subsequently delivered to the skin by diffusion.

Figure 2:
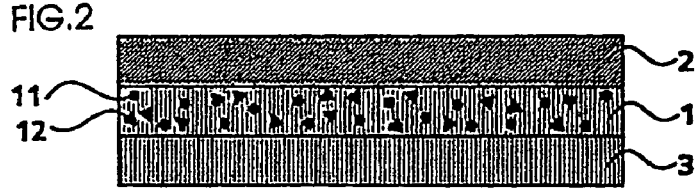

System A may alternatively be equipped with a control layer (3) (system B, FIG. 2).

The control layer either controls the absorption of moisture and thereby the activation itself, or alternatively the active substance release and thereby the release behaviour after activation. In the structure illustrated, the control layer simultaneously possesses pressure-sensitive adhesive properties and serves to fix the system on the skin.

Figure 3:
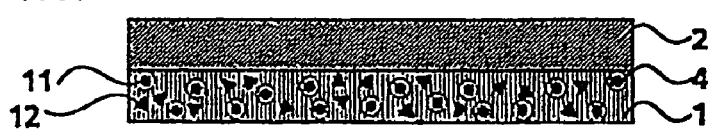
Figure 4:

Optionally, this control function can also be performed by a layer enveloping the active substance or the activator in dispersed state (systems C and D, FIGS. 3 and 4).

Figure 5:
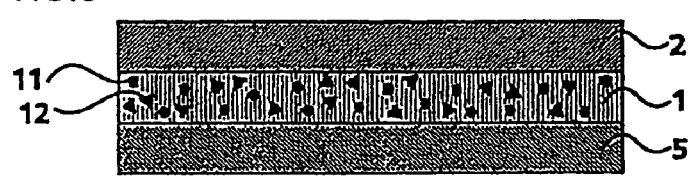

Should the active agent or the activator be incompatible with the pressure-sensitive adhesive layer, it is preferable to add a separate pressure-sensitive adhesive layer (5) on the side facing the skin (system E, FIG. 5). This addition of a pressure-sensitive adhesive layer is, by analogy, also applicable to systems A–D.

Figure 6:
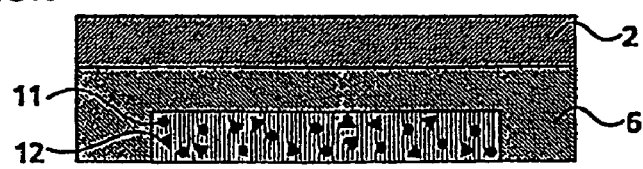

The additional pressure-sensitive adhesive layer does not need to be configured throughout the entire surface. The anchoring of the system on the skin may also be effected by a pressure sensitive adhesive layer (6) projecting outwardly beyond the reservoir layer (system F, FIG. 6). This procedure, too, is applicable to the systems A–D.

Figure 7:
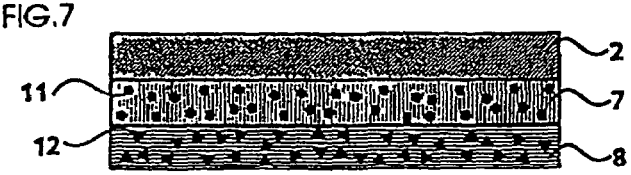
Figure 8:
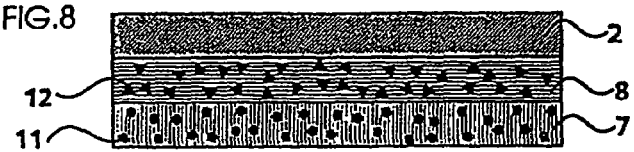

In order to obtain a certain activation or release behaviour, it may be necessary to incorporate the active agent and the activator in separate layers of the TTS. In the preferred case, one of these two reservoir layers, i.e. layer (7) containing the active substance or layer (8) containing the activator, is simultaneously the pressure-sensitive adhesive layer which enables the system to be anchored on the skin. Either the active substance is present in a layer nearer to the skin than that of the activator (system G, FIG. 7), or vice versa (system H, FIG. 8).

Figure 9:
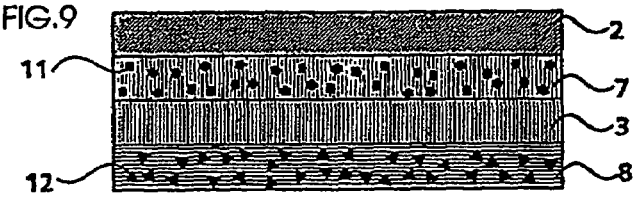

With structures of this kind, the activator is dissolved under absorption of moisture, diffuses into the neighbouring layer to the active substance, which is present in salt form, and liberates therefrom the base or acid. This free form then diffuses toward the skin and via the skin enters the body. Alternatively, dissolution of the active substance may occur, said active substance diffusing into the neighbouring layer towards the activator and being converted by said activator into the free base or acid. To control the access of active substance to the activator, or the reversed process, it may be useful to provide a control layer (3) which is arranged between the two reservoir layers for active substance and activator (system I, FIG. 9). The principle can, by analogy, also be applied to the system H.

Figure 10:
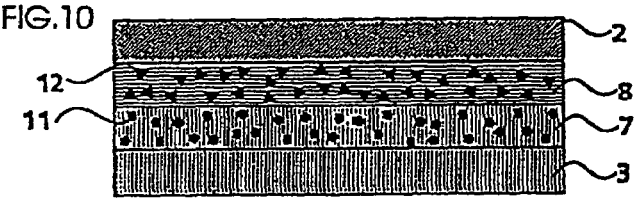

The control layer may also be provided as the layer (3) nearest to the skin and, if it also has pressure-sensitive adhesive properties, serve to anchor the entire system on the skin (system J, FIG. 10).

Figure 11:

Instead of introducing separate control layers, it is also possible to enclose the active substance or the activator in dispersed state with a control layer (4), by analogy to systems C and D (system K, FIG. 11).

Figure 12:
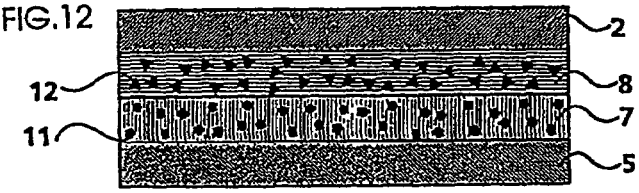

Should neither the active substance nor the activator be compatible with a suitable pressure-sensitive adhesive, it may be required to introduce a separate pressure-sensitive adhesive layer (5) (system L, FIG. 12).

This structure is by analogy, applicable to systems G–K.

Figure 13:
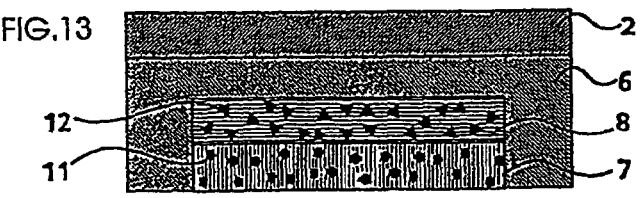

Finally, it is also possible to provide, instead of a full-surface skin-facing pressure-sensitive adhesive layer, a pressure-sensitive adhesive layer (6) which overlaps the reservoir layers only in the marginal areas, by analogy to system F (system M, FIG. 13). This approach, too, is, by analogy, applicable to systems G–K.

Preferably, a TTS constructed according to the present invention has the structure as described in the following: The overall construction follows FIG. 1. The active agent and the activating agent in their respective first chemical states are present as solids, dispersed side by side in a single matrix layer. This matrix layer has at the same time pressure-sensitive adhesive properties and serves to fix the system on the skin. The pressure-sensitive adhesive matrix is preferably based on a silicone rubber.

The active substance in its non-ionic form is a chemical base, and this basic form has little chemical stability. The activating agent in its first state is a basic-reacting substance; it is preferably an alkaline earth metasilicate or alkaline earth trisilicate in a hydrated form.

The backing layer of the TTS consists of an almost water vapour-impermeable film, preferably of polyethylene terephthalate (PET), or of a laminate of 2 layers of which one is made of PET.

The primary packaging of the TTS possesses a barrier action to water vapour that is as high as possible in order to prevent premature activation during storage.

EXAMPLES

1. Activators

Of the basic activators described, the silicates and phosphates are, due to their particular water-binding capacity, particularly suitable.

The dehydration behaviour of these substances was examined in three example substances by Difference Scanning Calorimetry (DSC). This thermal analysis provides information on the stages of dehydration taking place under energy absorption, and on the respective typical temperature.

Figure 14A:
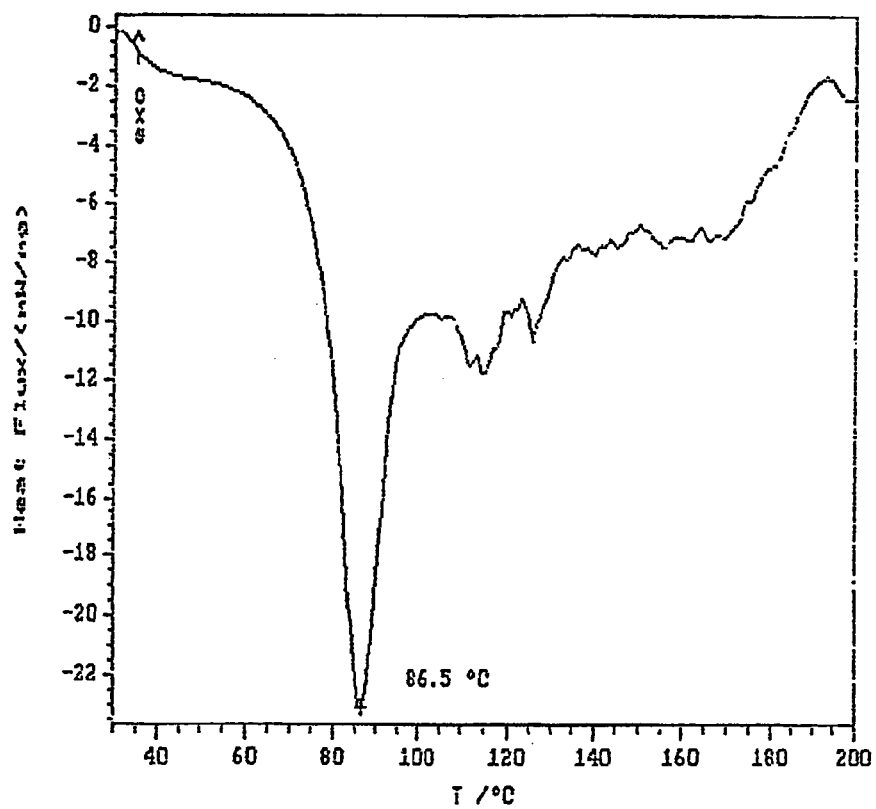
FIG. 14A depicts a dehydration profile of $Na_2SiO_3 \cdot 5H_2O$.
Figure 14B:
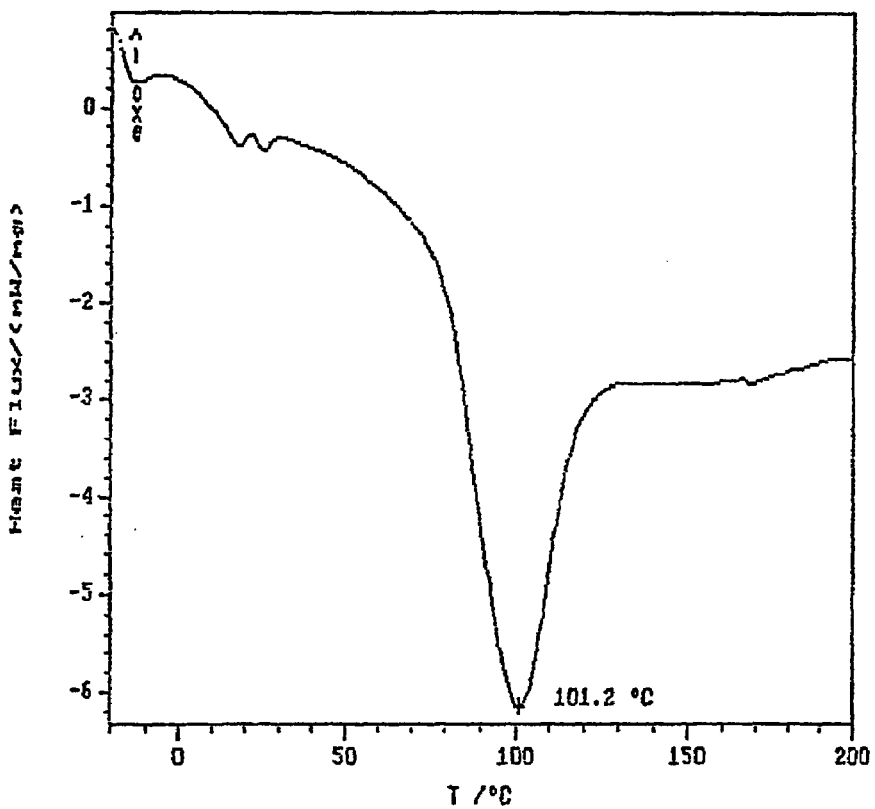
FIG. 14B depicts a dehydration profile of $Na_2Si_3O_7 \cdot xH_2O$.

$Na_2SiO_3.5H_2O$ dehydrates substantially at 86.5° C. (FIG. 14a). With $Na_2Si_3O_7.xH_2O$ this does not occur until 101.2° C. (FIG. 14b).

Figure 14C:
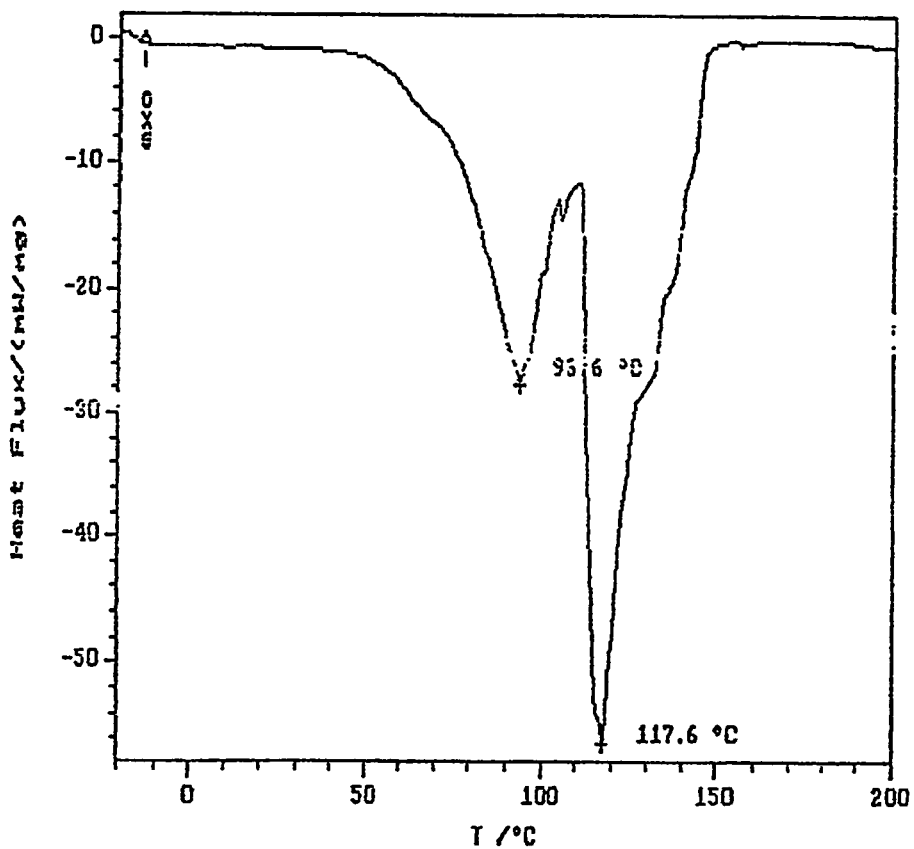
FIG. 14C depicts a dehydration profile of $Na_3PO_4 \cdot 12H_2O$.

In the case of $Na_3PO_4.12H_2O$ there is observed a multiple-stage dehydration which takes place mainly at 93.6° C. and 117.6° C. (FIG. 14c).

2. Transdermal Therapeutic System (TTS)

All of the activating agents and therapeutic agents used in the example systems were milled in a blade disintegrator and passed through a sieve of a mesh width of 50 μm prior to use. This was necessary in order to be able to spread the preparations in thin layers and to achieve a uniform distribution in the finished product.

2.1. Example TTS Comprising SDZ ENA713 as Active Agent

An example TTS was developed for delivery of the active substance SDZ ENA713 to the skin. SDZ ENA713 is a research substance of the firm of Novartis for treatment of Alzheimer's disease.

The basic substance was utilized in form of the hydrogen tartrate salt. In a structure corresponding to system A, this active substance salt was incorporated, along with the activator sodium metasilicate, into a silicone-based pressure-sensitive adhesive.

Composition of the pressure-sensitive adhesive layer (%–wt. of dried matrix):

| Formulation | I | II | III |
|---|---|---|---|
| ENA 713 Hydrogen Tartrate | 10 | 10 | 10 |
| $Na_2SiO_3$ | — | 3 | — |
| $Na_2SiO_3.5H_2O$ | — | — | 3 |
| Bio-PSA Q7-4301 | 90 | 87 | 87 |

Bio-PSA Q7-4301 is a medicinal pressure-sensitive adhesive on the basis of polydimethyl siloxane (Dow Corning).

The active substance and, optionally, the activator were added to the solution of the adhesive in benzine. By stirring, a homogenous dispersion was obtained. This dispersion was coated on a suitable flat-shaped carrier (in the example: ScotchPak 1022—a polyethylene terephthalate film by the firm of 3M with a dehesive coating on basis of fluorinated polymers).

Drying took place for 10 minutes at room temperature and for 10 minutes at 50° C., in an exhaust air drying cupboard. The weight per unit area of the matrix was typically 60 g/m².

The exposed side of the dried matrix was laminated with a suitable film (in the example: Hostaphan RN 15—a polyethylene terephthalate film by Hoechst).

Formulations I–III were used in in-vitro permeation tests on the model of bovine udder skin (n=3). Static, two-chamber diffusion cells of the modified Franz cell type as generally known in the field of TTS research and development were used.

Figure 15:
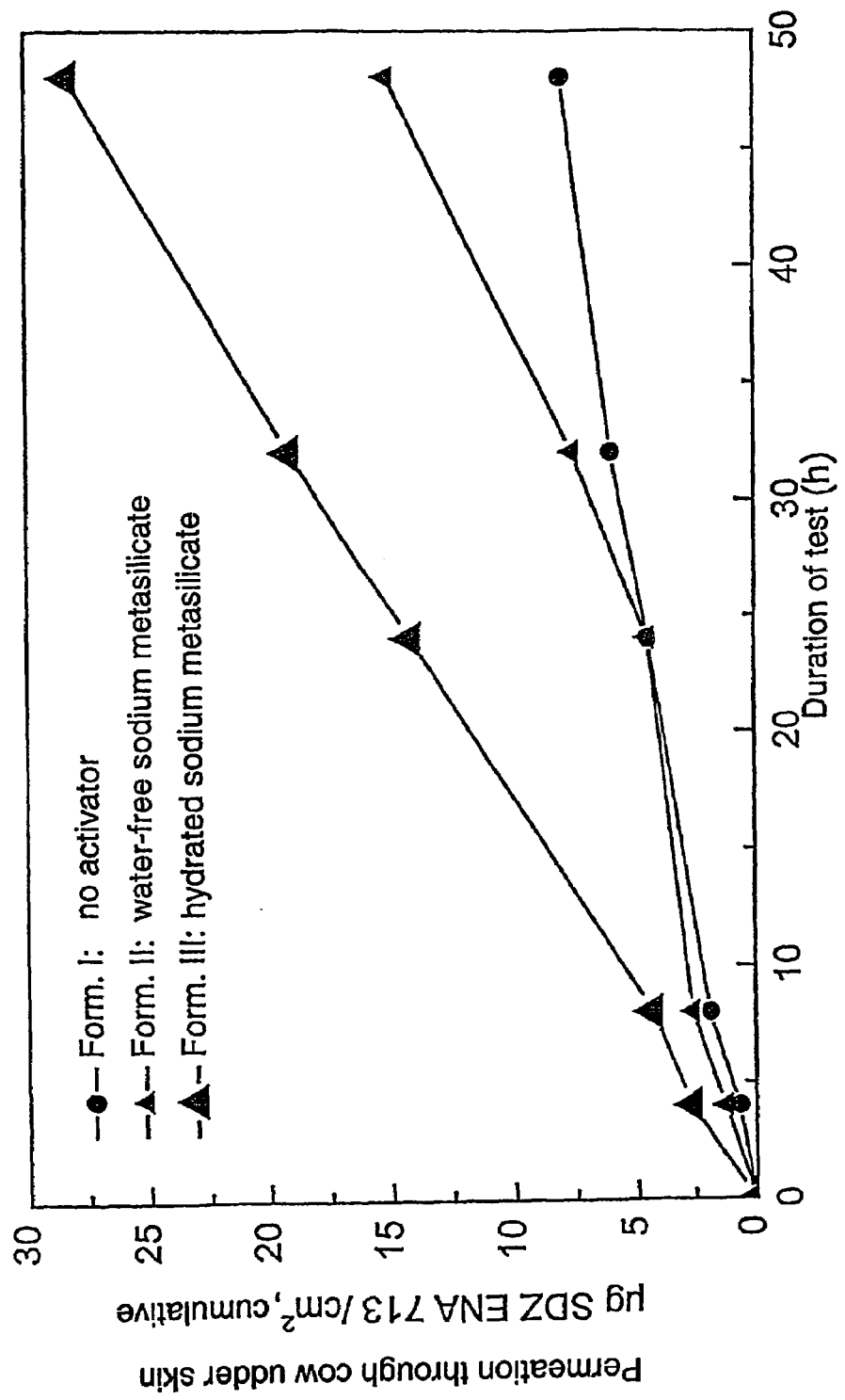
FIG. 15 depicts a permeation profile of therapeutic systems with and without an activator.

The resultant permeation profiles are shown in FIG. 15. Whilst the active substance salt without activator salt is released only in a very small amount, under the influence of the activators a controlled permeation takes place. In the hydrated state (pentahydrate), the activator here leads to a markedly earlier onset of the active substance release and to an overall active substance release higher than that obtained by the water-free activator.

2.2 Example TTS Comprising Ropinirole as Active Substance

Ropinirole is a basic active agent by SmithKline Beecham for treating Parkinson's disease. In the form of its free base, ropinirole is chemically very unstable and is therefore hardly suitable for processing and storage in a TTS.

A moisture-activatable TTS was developed containing the hydrochloride instead of the free base. As activators, sodium trisilicate and various basic sodium phosphates were tested.

Composition of the pressure-sensitive adhesive layer (%–wt of the dried matrix):

| Formulation | IV | V | VI | VII | VIII | IX |
|---|---|---|---|---|---|---|
| Ropinirole HCl | 10.0 | 10.0 | 10.0 | 10.0 | 10.0 | 10.0 |
| $Na_2Si_3O_7$ | — | — | — | — | — | 6.0 |
| $Na_2Si_3O_7.XH_2O$* | 6.0 | — | — | — | — | — |
| $Na_2SiO_3.5H_2O$ | — | 5.2 | — | — | — | — |
| $Na_2HPO_4.2H_2O$ | — | — | 6.0 | 3.0 | — | — |
| $Na_3PO_4.12H_2O$ | — | — | — | 6.4 | 6.4 | — |
| Isopropyl Myristate | 1.0 | 1.0 | 1.0 | 1.0 | 1.0 | 1.0 |
| Bio-PSA Q7-4301 | 83.0 | 83.3 | 83.0 | 79.6 | 82.6 | 83.0 |

*The bound water corresponds to 10%-wt. of the substance.

The active substance and possibly the activator were added to the solution of the adhesive in benzine, into which the liquid isopropyl myristate had been added previously. A homogenous suspension was obtained by stirring.

This suspension was coated on an appropriate flat carrier (in the example: ScotchPak 1022).

Drying took place for 10 minutes at room temperature and for 10 minutes at 80° C., in an exhaust air drying cupboard. The weight per unit area of the dried matrix was typically 60 g/m².

The exposed side of the dried matrix is laminated with a suitable film (in the example: Hostaphan RN15)

Formulations IV–VIII were used in in-vitro permeation tests on human full-thickness skin in modified Franz cells (n=3).

Figure 16:
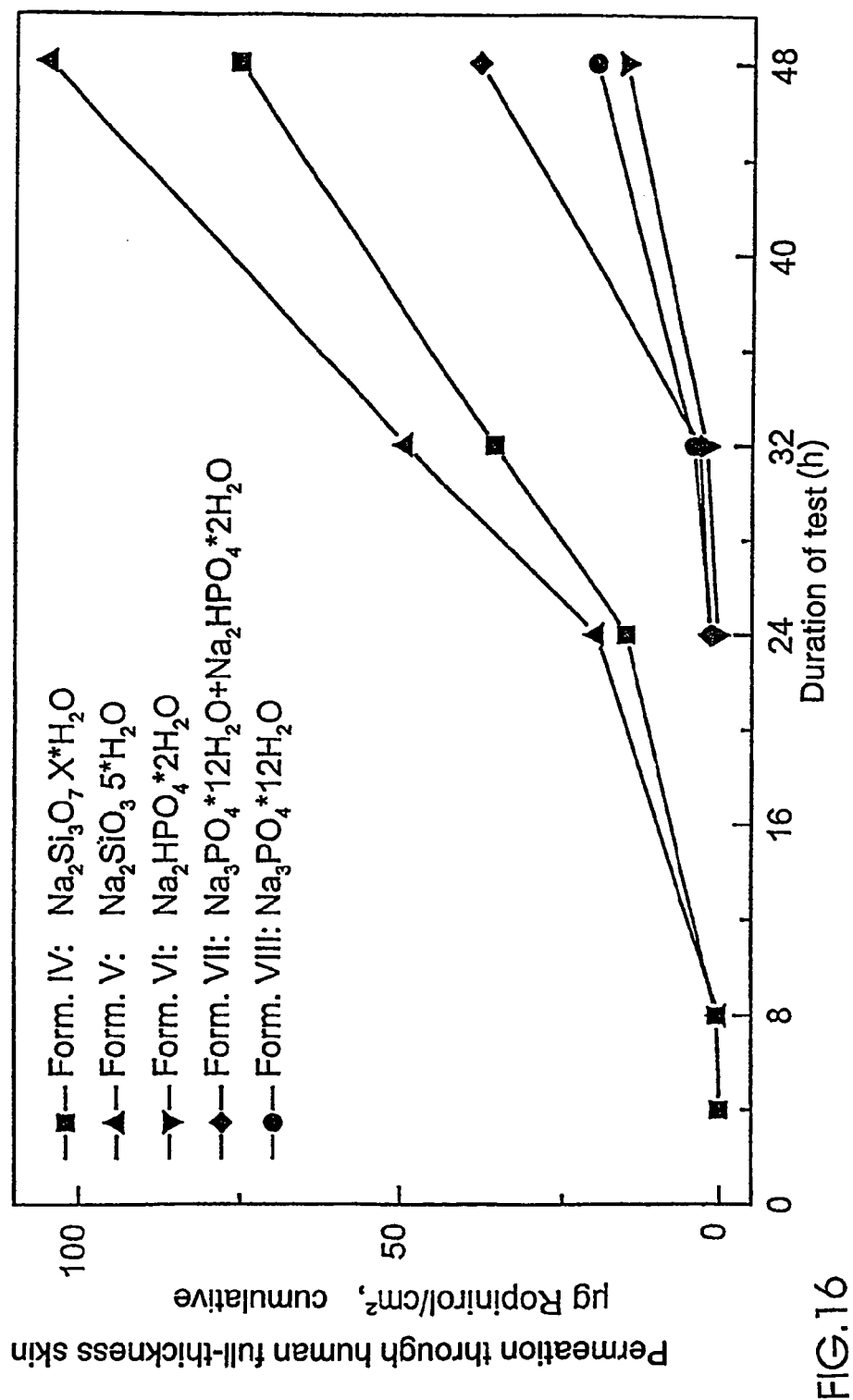
FIG. 16 depicts a permeation profile of various embodiments of the therapeutic systems of the invention.

The resultant permeation profiles are shown in FIG. 16. As activators, the silicates used generally prove to be clearly superior to the phosphates.

Of the phosphate-containing formulations, the mixture of the two basic phosphates (VII) surprisingly yields the best results, although the pure triphosphate (VIII) should react more strongly basic under moisture absorption and should thus cause a stronger activation of ropinirole.

The further examination showed that the hydrate water content in the sodium trisilicate has a clearly positive effect on the activator function.

If this auxiliary agent is dehydrated for 2 hours at 130° C. prior to its use (formulation IX), the activation process is delayed.

Figure 17:
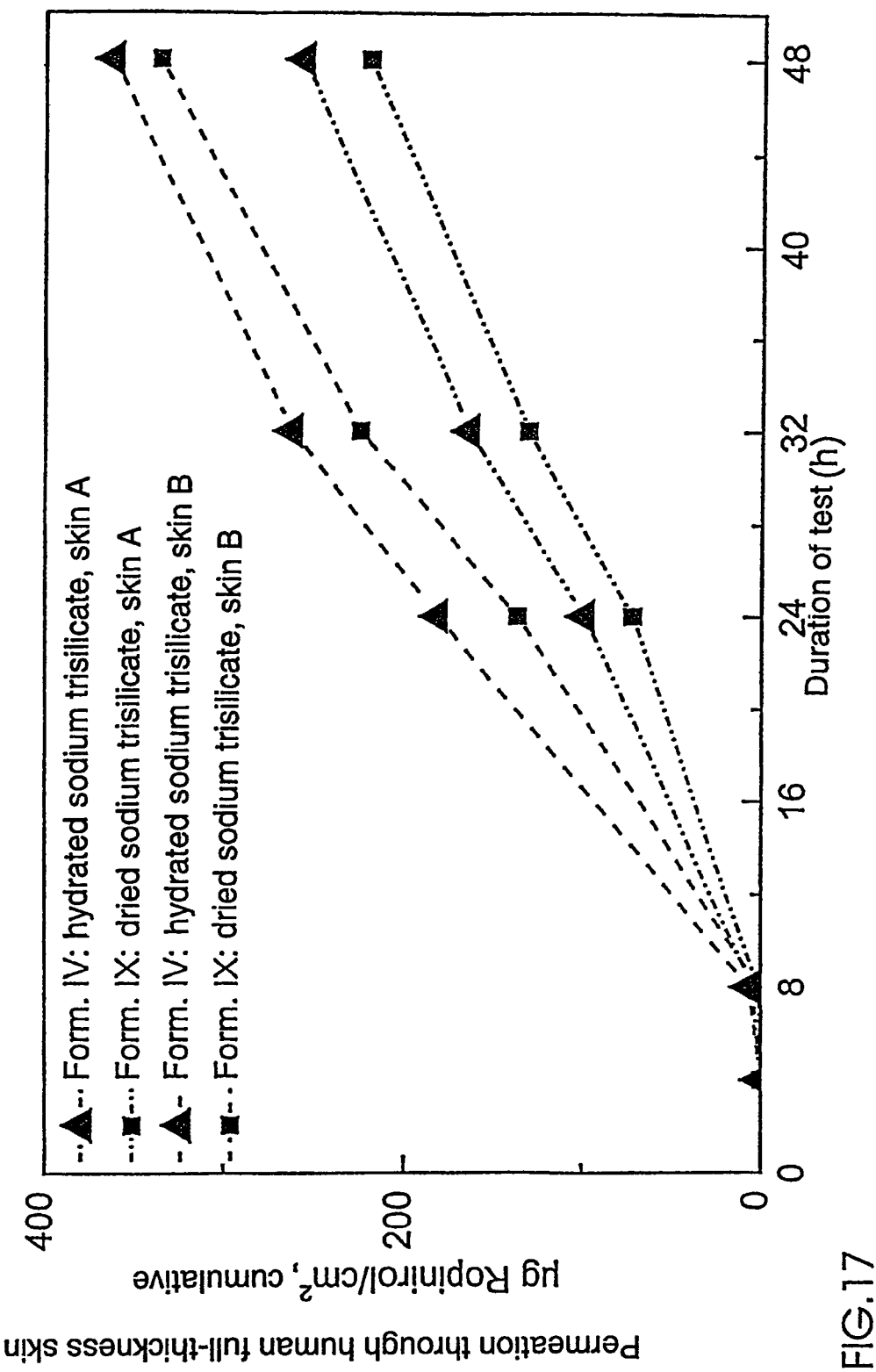
FIG. 17 depicts a permeation profile comparing the effects of hydrated and dried activator.

This finding could be confirmed in vitro on human full-thickness skin of 2 different individuals (n=3; FIG. 17). The hydrate water content alone caused an increase in permeation after 24 hours by 33% and 37%, respectively, as compared to the water-free form of the activator.

Conventional and moisture-activatable TTSs with ropinirole as active substance were examined as to stability.

The following formulations were tested:

| Formulation | X | XI | XII | XIII |
|---|---|---|---|---|
| Ropinirole Base | 8.0** | — | — | — |
| Ropinirole HCl | — | 6.3** | 10.0 | 10.0 |
| Na$_2$Si$_3$O$_7$.XH$_2$O* | — | 2.9 | 6.0 | — |
| Na$_2$HPO$_4$.2H$_2$O | — | — | — | 3.0 |
| Na$_3$PO$_4$.12H$_2$O | — | — | — | 6.4 |
| Isopropyl Myristate | 2.0 | 2.0 | 2.0 | 2.0 |
| Bio-PSA Q7-4301 | 90.0 | 88.8 | 82.0 | 88.6 |

*The bound water corresponds to 10%-wt. of the substance.
**The active substance content of the formulations containing dissolved free base is dependent on the maximum amount to be introduced in the respective process. In the case of crystalline-suspended active substance salt, the content was arbitrarily chosen to be 10%.

Formulation X was prepared by emulsifying oily ropinirole base in the benzine adhesive solution, and by coating and drying this solution.

Ropinirole base was initially isolated from the hydrochloride salt as follows:

A solution of 10.0 g of ropinirole hydrochlorid in 100 ml of water was adjusted to a pH of 10–11 by dripping in 5 N aqueous NaOH solution.

This solution was extracted twice in succession with 50 ml of diethyl ether at a time; the two ether phases were united.

The ethereal solution of ropinirole base was dried with water-free Na$_2$SO$_4$, filtered off and subsequently narrowed down to dryness in a nitrogen stream.

The oily residue was redried and finally left to crystallise in the refrigerator at 4° C. This yielded 8.94 g of ropinirole base or 99% of the theory. The melting point was determined at 73° C. (DSC), purity was 98% (HPLC).

With formulation XI, ropinirole HCl and sodium trisilicate were initially mixed with a small amount of ethanol and left to react for 18 hours at room temperature and under absence of light, while stirring. This pre-solution was then mixed in a corresponding amount with the benzine solution of the adhesive, coated and dried.

The preparation of formulations XII and XIII is analogous to the preparation of formulations IV to VIII.

Concerning the conditions of coating and drying as well as the film materials used in formulations X to XIII, reference is likewise made to formulations IV to VIII.

Figure 18:
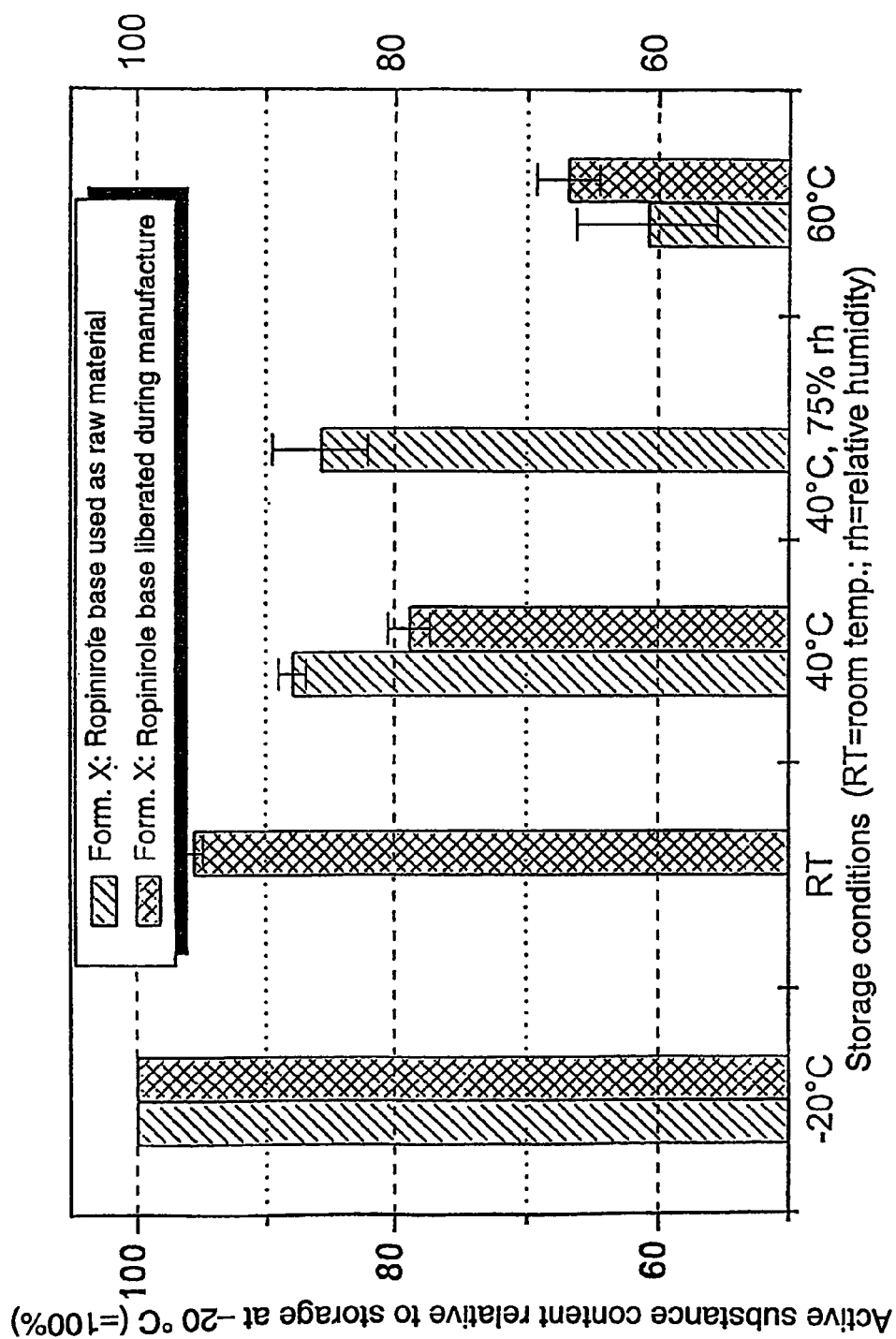
FIG. 18 depicts the stability of ropinirole without activator.

Already after one month's storage, the following picture results (n=6):

The free base ropinirole proves to be too unstable for a marketable product (formulation X, FIG. 18), even if a pure silicone adhesive without further additives is used.

Figure 19:
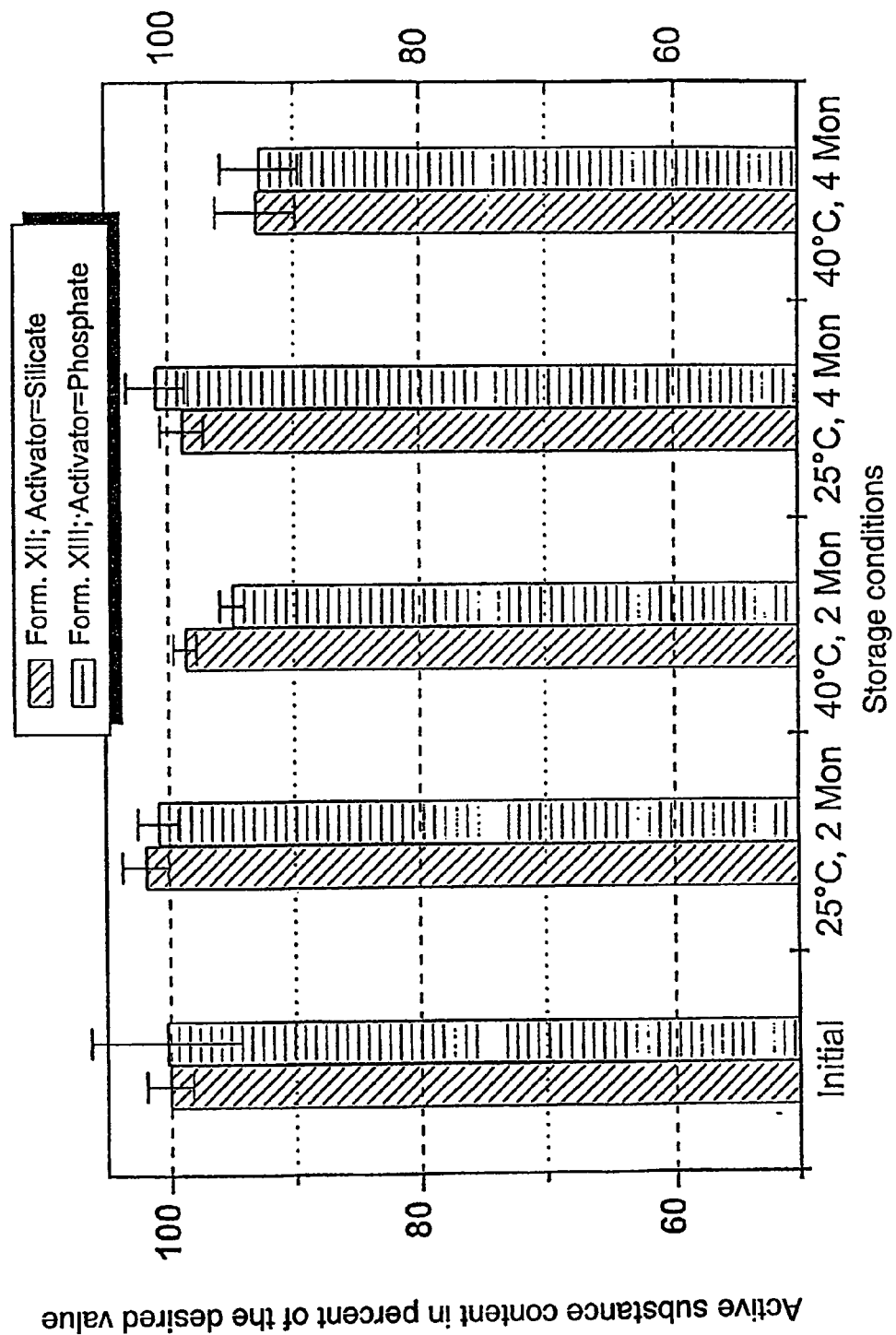
FIG. 19 depicts the stability of ropinirole with activator.

This also applies if ropinirole is utilised in the salt form of the hydrochloride but the base is released therefrom by the activator already during the manufacture of the TTS (formulation XI, FIG. 19).

If aqueous sodium trisilicate is used, the presence of ethanol (which in usual quality always contains small amounts of water) already suffices to trigger the conversion of ropinirole hydrochloride into the base. This reaction, which takes place readily, leads to the realization that for preparing the TTS according to the invention, there should be utilised aprotic solvents which are as nonpolar as possible. In this manner it is possible to prevent an unwanted premature onset of the transformation of the active substance salt into the base. Such solvents are preferably ethyl acetate, pentane, hexane, cyclohexane, heptane, octane, toluol and xylol, dichloromethane and chloroform as well as benzine of various boiling ranges.

The moisture-activatable formulations XII and XIII, prepared in benzine solution, according to the data show a considerably improved stability which is sufficient for a marketable product (n=6, FIG. 19) after 2 and 4 months of storage. Obviously, the release of the base only takes place to a negligible extent, if at all, during the manufacture of the TTS.

With formulations comprising ropinirole as active substance it was further found that the course of moisture activation can obviously be modified by small amounts of certain additives. Thus, addition of very small amounts of isopropyl myristate already causes accelerated activation and correspondingly increased overall permeation in vitro. The following formulations were tested on bovine udder skin in vitro (n=3):

| Formulation | XIV | XV | XVI | XVII | XVIII |
|---|---|---|---|---|---|
| Ropinirole HCl | 10.0 | 10.0 | 10.0 | 10.0 | 10.0 |
| Na$_2$Si$_3$O$_7$.XH$_2$O* | 6.0 | 6.0 | 6.0 | 6.0 | 6.0 |
| Isopropyl Myristate | — | 0.5 | 1.0 | 2.0 | 4.0 |
| Bio-PSA Q7-4301 | 84.0 | 83.5 | 83.0 | 82.0 | 80.0 |

*The bound water corresponds to 10%-wt. of the substance.

The manufacture was performed according to the indications made with respect to formulations IV to VIII.

Figure 20:
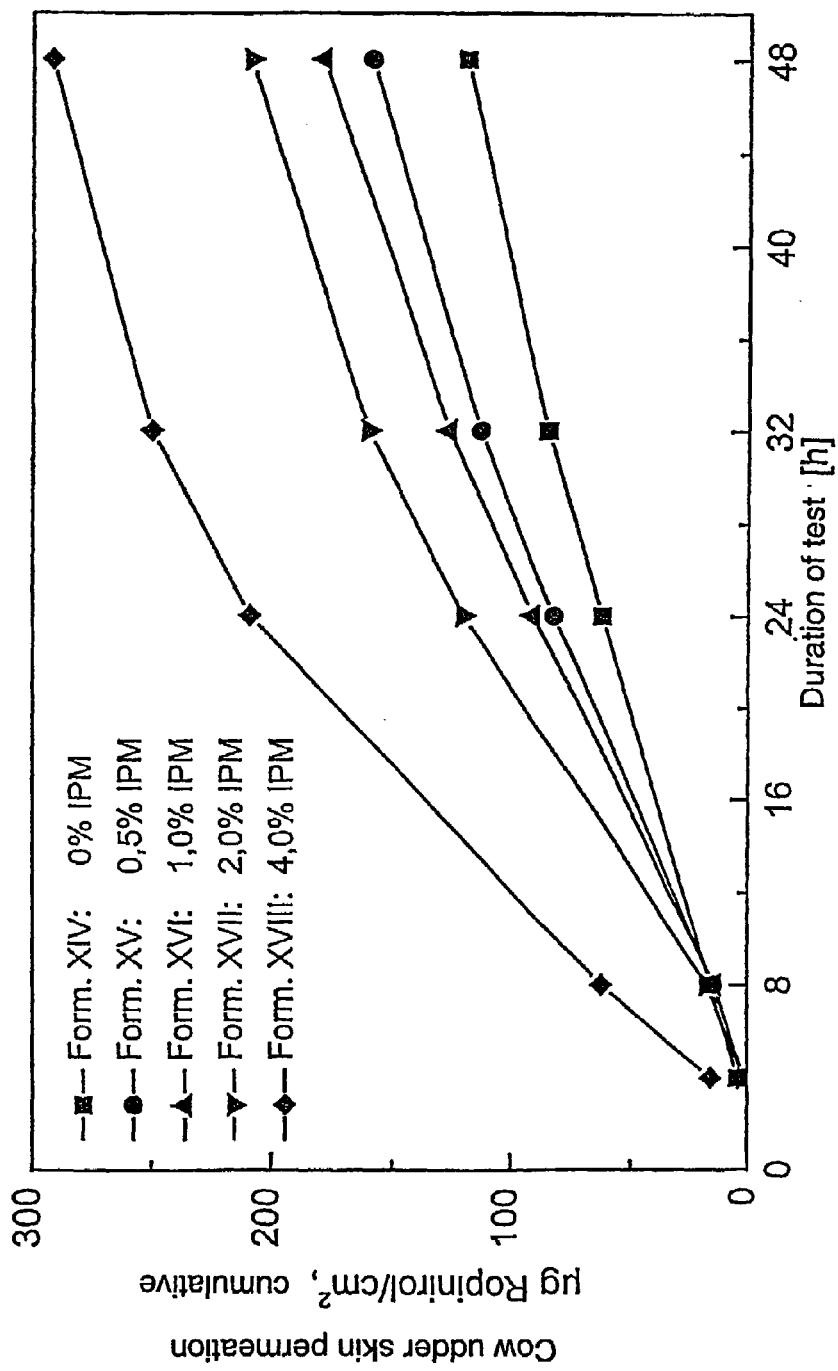
FIG. 20 depicts the effect of various concentrations of isopropyl myristate on a permeation profile of ropinirole.

The result shows that surprisingly small additions of isopropyl myristate already lead to accelerated activation. The effect is clearly correlated with the quantity of isopropyl myristate (FIG. 20).

Although in the past, isopropyl myristate as permeation enhancer has been observed and described in many cases, such an effect influencing the condition of the skin has hitherto never been found for concentrations of only 0.5%. What is more likely is an effect modulating the acid-base reaction which takes place under access of moisture, which effect can be utilised here. As a consequence, there is the possibility of modulating the moisture-activatable systems according to the invention by using appropriate additives in the course of activation.

The invention claimed is:

1. A therapeutic system for timed and controlled release of at least one therapeutic active agent to a human or animal organism by means of diffusion through the skin or mucous membrane,
said active agent initially being present, for the purpose of manufacture and storage,
in a first state in which it is chemically stable and insufficiently permeable for the skin or mucous membrane,
whereas it is converted at the application site into a second state by access of moisture, in which state it is suitable for diffusion through the skin or mucous membrane and in which it is taken up by the organism,
wherein said active agent in said first state is contained in the system as a pharmaceutically acceptable acid salt which is present dispersed as an undissolved solid and which upon access of emerging skin or mucous moisture and by a basic activating agent, which is likewise contained in the system, is chemically converted into the said second state of a base which is taken up through the skin or mucous membrane into the organism in an accelerated manner and in greater quantities compared to the acid salt form,
said basic activating agent is selected from a hydrated but undissolved form of a base consisting of sodium trisilicate, sodium metasilicate, disodium phosphate (secondary sodium phosphate), trisodium phosphate (tertiary sodium phosphate), tripotassium phosphate, magnesium carbonate hydroxide, aluminium magnesium hydroxide sulfate, trisodium citrate dehydrate, magnesium citrate tetradecahydrate, tetrasodium edentate dehydrate, potassium sodium tartrate tetrahydrate and disodium succinate hexahydrate,
wherein said basic activating agent has either intercalated or bound water of at least 5% to about 60% in its solid body structure.

2. The therapeutic system according to claim 1, characterized in that the moisture present at the application site is a liquid which is actively released by the skin via the sweat glands, or water vapor which is passively released in the form of a gas via the skin surface, and that in the case of mucous membranes, said moisture are body liquids secreted by glands.

3. The therapeutic system according to claim 1, characterized in that the therapeutic active agent is present in an amount of 0.5 to 50%, of the overall weight.

4. The therapeutic according to claim 1, characterized in that the ratio of activating agent to the therapeutic agent is 0.1 to 10, relative to the stoichiometry of the chemical reaction.

5. The therapeutic system according to claim 1, characterized in that both the therapeutically active agent and the activating agent are contained in substantially undissolved form.

6. The therapeutic system according to claim 5, characterized in that agents present in undissolved form have a particle size of between 1 and 200 µm.

7. The therapeutic system according to claim 6, characterized in that the therapeutic agent and the activating agent are uniformly dispersed in a matrix, wherein the matrix is a layer of the transdermal therapeutic system.

8. The therapeutic system according to claim 7, characterized in that a matrix layer or a control layer possesses pressure-sensitive adhesive or mucoadhesive properties.

9. The therapeutic system according to claim 6, characterized in that the therapeutic active agent and the activating agent are present in separate matrix layers.

10. The therapeutic system according to claim 9, characterized in that one of the two matrices is in direct contact with the skin or mucous membrane.

11. The therapeutic system according to claim 10, characterized in that the matrix layer intended for contact with the skin possesses pressure-sensitive adhesive or mucoadhesive properties.

12. The therapeutic system according to claim 1, characterized in that it further comprises a control layer which is free of the therapeutically active agent and the activating agent.

13. The therapeutic system according to claim 12, characterized in that the control layer is arranged such that it is in direct contact with the skin or mucous membrane when the system is applied.

14. The therapeutic system according to claim 12, characterized in that the control layer is configured and arranged such that it controls the extent and speed of the absorption of moisture from the site of application into the system.

15. The therapeutic system according to claim 12, characterized in that the control layer is configured and arranged such that it controls the extent and speed of the diffusion of the therapeutically active agent in its activated form out of the system to the application site.

16. The therapeutic system according to claim 12, characterized in that the control layer is inserted between the therapeutically active agent and the activating agent.

17. The therapeutic system according to claim 12, characterized in that the control layer constitutes a plurality of spherical single layers of identical composition which envelope the undissolved, dispersed therapeutically active agent or the undissolved, dispersed activating agent.

18. The therapeutic system according to claim 12, characterized in that the control layer is configured and arranged such that it controls the extent and speed of the diffusion of the activating agent in its dissolved form towards the therapeutically active agent.

19. The therapeutic system according to claim 12, characterized in that the control layer is configured and arranged such that it controls the extent and speed of the diffusion of the therapeutically active agent in its dissolved form towards the activating agent.

20. The therapeutic system according to claim 1, characterized in that the therapeutically active agent is ropinirole hydrochloride or another pharmaceutically acceptable salt of ropinirole.

21. The therapeutic system according to claim 6, characterized in that the matrix layer consists of a formulation based on silicone rubber, polyisobutylene, polyisoprene, or a block copolymer of styrene with isoprene or butadiene.

22. The therapeutic system according to claim 3, wherein the amount of therapeutic agent is 1.0 to 20% of the overall weight.

23. The therapeutic system according to claim 4, wherein the ratio is 0.2 to 2.0.

24. The therapeutic system according to claim 6, wherein the particle size is between 2 and 50 µm.

25. The therapeutic system according to claim 6, characterized in that the therapeutic agent is substantially dissolved upon access of moisture and then diffuses to the activating agent within the therapeutic system where said therapeutic agent is converted into the form of the acid or base, which chemically corresponds to the pharmaceutically acceptable salt of the therapeutic agent, by the activating agent.

26. The therapeutic system according to claim 6, characterized in that the activating agent, which is present as a pharmaceutically acceptable salt, is substantially dissolved and then diffuses to the therapeutic agent within the therapeutic system, where said activating agent converts said therapeutic agent into the form of the acid or base, which chemically corresponds to the pharmaceutically acceptable salt of said therapeutic agent.

27. The therapeutic system according to claim 1, wherein said therapeutic system further comprises a fatty acid ester of a short-chain alcohol in an amount between 0.5 and 5.0% by weight.

28. The therapeutic system according to claim 27, characterized in that the esters are formed from a saturated or mono-unsaturated carboxylic acid with 6 to 18 carbon atoms and an alcohol with 1 to 3 carbon atoms having maximally one hydroxyl group per carbon atom.

29. The therapeutic systems according to claim 28, wherein the alcohol molecule is further esterified and the ester is isopropyl myristate, isopropyl palmitate, a saturated triglyceride, glycerin monolaurate or glycerin monoleate.

* * * * *